US00PP12920P2

(12) United States Plant Patent
Delbard

(10) Patent No.: US PP12,920 P2
(45) Date of Patent: Sep. 3, 2002

(54) SPRAY ROSE PLANT NAMED 'DELSPORG'

(75) Inventor: Guy Delbard, Hyeres (FR)

(73) Assignee: Société Anonyme des Pépiniéres et Roseraties Georges Delbard, Commentry (FR)

( * ) Notice: Subject to any disclaimer, the term of this patent is extended or adjusted under 35 U.S.C. 154(b) by 0 days.

(21) Appl. No.: 09/588,744

(22) Filed: Jun. 6, 2000

(30) Foreign Application Priority Data

Jan. 10, 2000 (FR) ..... 17058

(51) Int. Cl.[7] ..... A01H 5/00
(52) U.S. Cl. ..... Plt./102
(58) Field of Search ..... Plt./102, 108, 131, Plt./142

*Primary Examiner*—Bruce R. Campell
*Assistant Examiner*—June Hwu
(74) *Attorney, Agent, or Firm*—Burns, Doane, Swecker & Mathis, L.L.P.

(57) ABSTRACT

A new and distinct variety of *Rosa hybrida* Spray rose plant is provided which abundantly forms clusters of attractive double flowers on a substantially continuous basis that are bicolored orange and pinkish-white. The plant is well suited for cut flower production under greenhouse growing conditions. The flowers are long lasting. The plant exhibits an upright to bushy growth habit, forms vigorous vegetation, and is well suited for greenhouse forcing for commercial rose production. Additionally, the plant has proven to be resistant to common rose diseases when grown under greenhouse growing conditions.

1 Drawing Sheet

SUMMARY OF THE INVENTION

The new variety of *Rosa hybrida* Spray rose plant of the present invention was created by artificial pollination wherein two rose parents were crossed which previously had been studied in the hope that they would contribute the desired characteristics. The female parent (i.e. the seed parent) of the new variety was an unnamed rose seedling. The male parent (i.e., the pollen parent) of the new variety also was another unnamed rose seedling. Neither parent plant was patented in the United States. The parentage of the new variety can be summarized as follows:

Unnamed Rose Seedling×Unnamed Rose Seedling.

The seeds resulting from this cross pollination were sown and 245 small plantlets were obtained which were physically and biologically different from each other. Selective study resulted in the identification of a single plant of the new variety.

It was found through careful study that the new Spray rose variety of the present invention can be characterized by the following combination of characteristics:

(a) from a physical point of view forms medium green mature wood, assumes an upright to bushy growth habit, and forms attractive long-lasting clusters of bicolored orange and pinkish-white double flowers, and (b) from the biological point of view it forms vigorous vegetation, produces flowers in abundance, exhibits the ability readily to be forced, and is resistant to diseases when grown under greenhouse growing conditions.

The new variety well meets the needs of the horticultural industry and is particularly well suited for growing in the greenhouse for the commercial production of attractive clusters of long-lasting cut flowers.

The new variety can be readily distinguished from other spray rose varieties in view of the combination of characteristics described herein. For instance, the well-known 'Interniki' U.S. Plant Pat. No. 8,114 spray rose variety forms blossoms of a uniform red coloration unlike the bicolored blossoms of the new variety of the present invention, forms leaflets having a sharper apex, and forms thorns of a paler purple coloration. The stems of the new variety are long and straight and commonly bear approximately 5 to 21 blossoms per cluster. The vase life of the distinctive orange and pinkish-white bicolored flowers is long.

The new variety has been found to undergo asexual propagation and can be readily reproduced by conventional routes, such as budding (i.e., eye grafting). This asexual reproduction as performed in the South of France has demonstrated that the combination of characteristics of the new variety is strictly transmissible from one generation to another and is firmly fixed.

The new variety has been named the 'Delsporg' variety.

BRIEF DESCRIPTION OF THE PHOTOGRAPH

The accompanying photograph shows as nearly true as it is reasonably possible to make the same in a color illustration of this character typical specimens of the plant parts of the new variety when grown in greenhouses in the South of France. The plants were approximately eleven months of age and were observed during March, 2000.

FIG. 1—illustrates a specimen of a flowering stem;

FIG. 2—illustrates a specimen of a main branch;

FIG. 3—illustrates a specimen of a young shoot with foliage, seven buds and an open flower;

FIG. 4—illustrates a specimen of a young shoot where primarily foliage is shown;

FIG. 5—illustrates from left to right four unattached specimens of a leaf with 7 leaflets—plan view—under surface; a leaf with 7 leaflets—plan view—upper surface; a leaf with 5 leaflets—plan view—upper surface; and a leaf with 3 leaflets—plan view—upper surface;

FIG. 6—illustrates from top to bottom specimens of a fully open flower—plan view reverse (left) and—plan view obverse (right); a pair of open flowers—plan view obverse; a pair of flowers in the course of opening shown from the side (left) and obverse (right); and a pair of floral buds at the opening of the sepals (left) and a pair of buds at the opening of the petals (right).

FIG. 7—illustrates specimens of a floral receptacle showing the arrangement of the stamens and pistils (left) and a floral receptacle showing the arrangement of the pistils with the sepals and stamens removed (right).

DETAILED DESCRIPTION

The chart used in the identification of the colors is that of The Royal Horticultural Society (R.H.S. Colour Chart). The description is based on the observation of plants grown in greenhouses in the South of France. The plants were approximately eleven months of age and were observed during March, 2000. The coloration in common terms sometimes also is provided.

Class: Spray rose.

Plant:

*Height.*—Plants which were pruned at a height of 1 m commonly produce floral stems having a lengths of approximately 40 to 80 cm (approximately 60 cm on average).

*Width.*—Approximately 50 to 60 cm.

*Habit.*—Upright to bushy.

Branches:

*Color.*—Young shoots: when approximately 20 cm in length, the side exposed to sunlight commonly exhibits a bronze coloration, Greyed-Orange Group 177A and 177B, with some green coloration, Yellow-Green Group 146C. The side away from the sunlight commonly is Yellow-Green Group 146B with some bronze coloration. Floral stems: Yellow-Green Group 146B with some bronze coloration. Mature wood: Medium green, Yellow-Green Group 146B and 146C.

*Thorns.*—Configuration: Upper edge: Slightly concave. Under edge: concave. Quantity: Short prickles typically are absent, and long prickles as indicated hereafter on 70 cm of stem commonly number approximately 13. Length: approximately 12 mm on average on floral stems and approximately 9 mm on average on mature wood, and commonly range from about 6 to 15 mm in length in each instance. Color: on a young shoots approximately 30 cm long, Greyed-Purple Group 184B and 184C; on floral stems Greyed-Purple Group 184C; and on mature wood Greyed-Orange Group 165A and 165B.

*Leaves.*—Number: typical for the class. Size: medium, and commonly measure approximately 10.5 to 13 cm in length and approximately 10.5 to 13 cm in width. Stipules: adnate, approximately 12 to 17 mm in length, approximately 4 to 8 mm (average approximately 6 mm) in width at the mid-point, approximately 7 to 10 mm (average approximately 9 mm) in width at the distal extremity, and normal for the class.

*Leaflets.*—Number: 1 to 7 on a 70 cm length stem with one leaflet rarely being present, approximately 1 or 2 three leaflets, approximately 1 or 2 five leaflets, and approximately 4 or 5 seven leaflets. Size: medium. Shape: at the base of terminal leaflet obtuse to rounded, and flat convex in cross section. Serration: present, medium, deep, and irregular. General appearance: smooth, medium glossy. Petiole: inner surface: grooved and commonly lacking a glandular edge. Petiole color on young shoot: bronze, Greyed-Orange Group 176A and 176B with reddish coloration on the inner surface and Yellow-Green Group 146D on the outer surface. Petiole color on floral stem: Yellow-Green Group 146D on the inner surface and Yellow-Green Group 146C on the outer surface. Petiole color on mature wood: Yellow-Green Group 146A and 146B on the inner surface and Yellow-Green Group 146C on the outer surface. Total Petiole Length: approximately 50 to 76 mm (average approximately 60 mm with a standard deviation of 2 mm). Terminal leaflet length: approximately 50 to 85 mm (average approximately 70 mm with a standard deviation of 5 mm). Terminal leaflet width: approximately 32 to 55 mm (average approximately 38 mm with a standard deviation of 2 mm). Terminal leaflet shape at base: obtuse to rounded. Terminal leaflet shape of apex: cuspidate. Leaflet color of young shoot: Yellow-Green Group 146A with purple serrations on the upper surface and Yellow-Green Group 146C at the center of the leaflets with reddish coloration and purple serrations on the under surface. Leaflet color on floral stem: Yellow-Green Group 147A on upper surface and Yellow-Green Group 147B on the under surface with glossiness of upper surface. Leaflet color of mature wood: Yellow-Green Group 147A on the upper surface and Yellow-Green Group 147B on the under surface.

Inflorescence:

*Number of flowers.*—Generally approximately 5 to 21 per stem in a cluster. Under greenhouse growing conditions it is most common to have approximately 10 flowers per stem.

*Peduncle.*—Yellow-Green Group 146B in coloration, slightly hairy, perfumed, and erect at the beginning of flowering and with some bending when the flowers are fully open. The length is approximately 50 mm for the central flower at the time of harvest.

*Sepals.*—Configuration: there commonly are two with medium to strong extensions, one with a medium extension, and two with a weak extension. The lengths commonly range from 10 to 24 mm. Color: Yellow-Green Group 146D on the upper surface, hairy with a small white edge, and Yellow-Green Group 146B on the under surface.

*Buds.*—Shape: ovate in longitudinal section just prior to the opening of the sepals. Size before the calyx breaks: approximately 22 to 24 mm (23 mm on average). Color as calyx breaks: blend of pink with Red Group 54B, and soon after the calyx breaks some orange coloration appears. Size as the first petals of the second row open: approximately 29 to 31 mm (average approximately 30 mm). Color as the first petals of the second row open: the inside coloration is orange and slightly darker than Red Group 40A, and the outside coloration at the base is White Group 155D and Red Group 54D to Red Group 55D on the edge sometimes suffused with pink of Red Group 54A.

*Flower.*—Time: in a greenhouse at a temperature of 16 to 25° C. the plant commonly blooms approximately 50 days during the winter. Shape: double arranged as a spray. Form: when viewed from above round to irregularly rounded, and when viewed from the side flattened convex. Diameter: medium to large, approximately 57 to 67 mm (approximately 62 mm on average with a standard deviation of 3 mm). Petal number: Commonly approximately 27 to 33 (approximately 30 on average). Petal size (second row from outside): the length is approximately 26 to 32 mm (approximately 29 mm on average with a standard deviation of 2 mm), and the width is approximately 23 to 30 mm (approximately 27 mm on average with a standard deviation of 3 mm). Petal shape: the first row of petals commonly exhibit a large obovate configuration, with weak to medium margin undulation, and strong reflexing at the margin. The petal apex and the petal base are rounded. Petal color: Central area of petals: on the outside pink, Red Group 56C, and finishing to white with pinkish coloration, and on the inside orange ranging from Red Group 40A to Red Group 44A commonly with a red vein with some variegation on some petals of White Group 155C and Red Group 38B. Margins of petals: on the outside pink, Red Group 56C, and on the inside orange ranging from Red Group 40A to Red Group 44A. Petal spot at base: Size: approximately 4 mm. Color on inner side: pale yellow, Yellow Group 4C. Color on outer side: pale yellow, Yellow Group 4D blended with some Red Group 56C. Petaloids: A few petaloids (e.g., 2 to 3 per bloom) commonly are present and may be fused to the stamens. They commonly are arched in configuration and possess a smooth texture. The size varies considerably. They commonly are 6 to 20 mm in length and 2 to 10 mm in width. Stamens: approximately 95 in number and somewhat regularly arranged below the level of the pistils. Filaments: located regularly around and slightly above the pistils, approximately 6 mm in length, and yellow of Yellow Group 4D in coloration. Anthers: approximately 1.5 mm in length, approximately 1 mm in width, and yellow, Yellow-Orange Group 16C with some Yellow-Orange Group 22A in coloration. Pollen: normal in quantity for the class and Yellow-Orange Group 15A in coloration. Pistils: approximately 25 to 60 in number (approximately 50 on average). Styles: approximately 5 mm in length and pale yellow, Yellow-Group 2D, in coloration with red spot below the stigma. Stigmas: Yellow Group 11C, and commonly extend slightly above the anthers. Receptacle: in longitudinal sectional configuration in the shape of a pitcher and at the open flower stage approximately 8 mm in length on average and approximately 8 mm in width on average. The coloration is Yellow-Green Group 144B. Hips: Orange Group 28A in coloration and commonly approximately 16 to 17 mm in diameter. Seeds: medium in size, approximately 8 to 12 in number (approximately 10 on average, and near Yellow Group 12D in coloration. Petal drop: petals detach cleanly. Fragrance: none, except for the fragrance of the hairy peduncle which commonly is apparent upon touching. Lasting quality: long with the flowers commonly lasting approximately 8 days when cut and placed in a vase.

Development:

*Vegetation.*—Vigorous.

*Blooming.*—Abundant, and substantially continuous under greenhouse growing conditions.

*Resistance to forcing.*—Good.

*Resistance to diseases.*—Good with respect to Powdery Mildew, Downy Mildew and Botrytis under greenhouse growing conditions.

I claim:

1. A new and distinct variety of Spray rose plant characterized by the following combination of characteristics:

(a) from a physical point of view forms medium green mature wood, assumes an upright to bushy growth habit, and forms attractive long-lasting bicolored clusters of orange and pinkish-white double flowers, and (b) from the biological point of view forms vigorous vegetation, produce flowers in abundance, exhibits the ability readily to be forced, and is resistant to diseases when grown under greenhouse growing conditions;

substantially as herein shown and described.

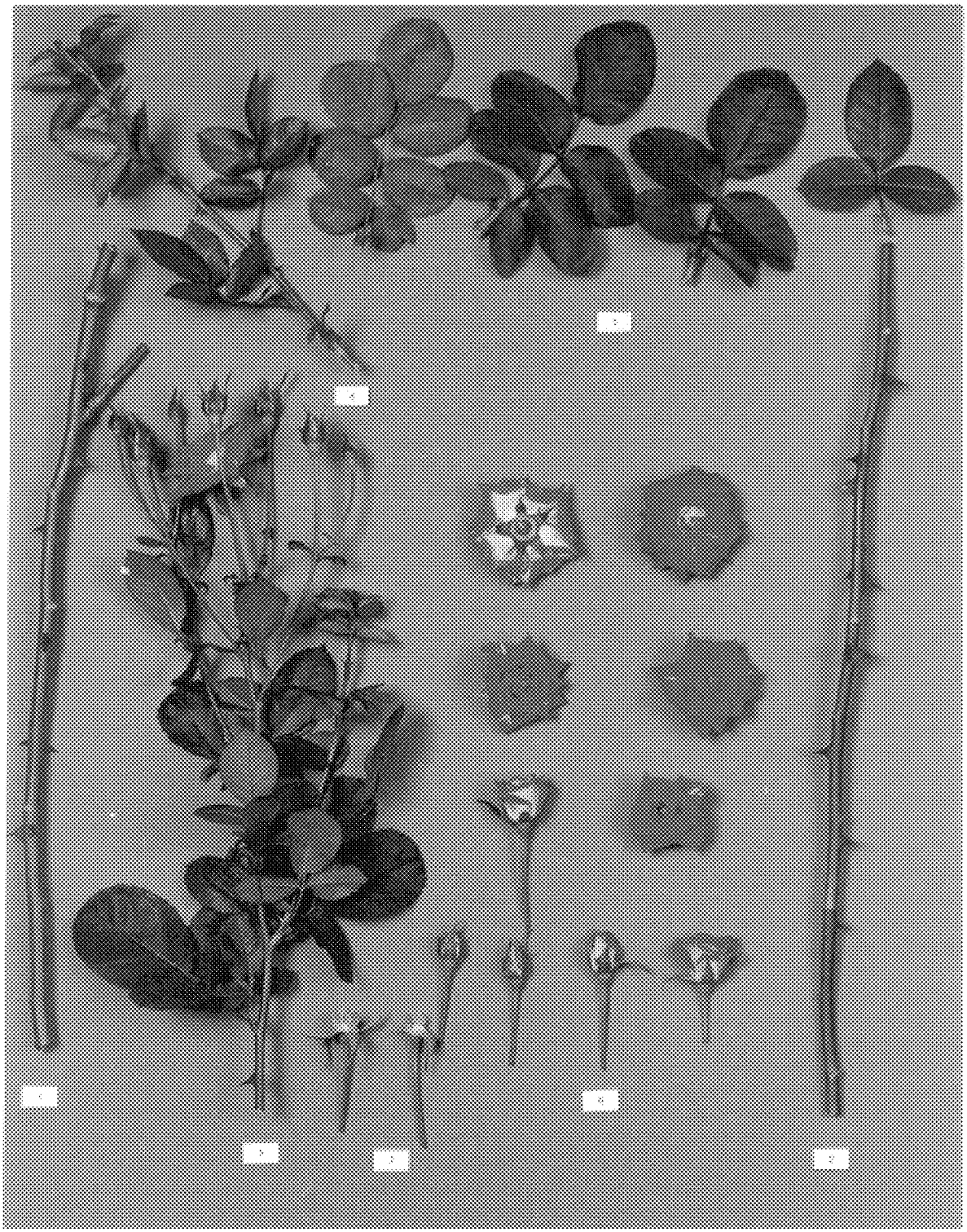

* * * * *